US007160831B2

(12) United States Patent
Vaughn et al.

(10) Patent No.: US 7,160,831 B2
(45) Date of Patent: *Jan. 9, 2007

(54) MOLECULAR SIEVE CATALYST COMPOSITION, ITS MAKING AND USE IN CONVERSION PROCESSES

(75) Inventors: Stephen N. Vaughn, Kingwood, TX (US); Yun-feng Chang, Houston, TX (US); Luc R. M. Martens, Meise (BE); Kenneth R. Clem, Humble, TX (US); Machteld M. Mertens, Boortmeerbeek (BE); Albert E. Schweizer, Midland, MI (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/178,374

(22) Filed: Jun. 24, 2002

(65) Prior Publication Data

US 2003/0018229 A1 Jan. 23, 2003

Related U.S. Application Data

(60) Provisional application No. 60/302,462, filed on Jul. 2, 2001.

(51) Int. Cl.
B01J 29/06 (2006.01)

(52) U.S. Cl. .................. 502/64; 502/68; 502/208; 502/214

(58) Field of Classification Search ................ 502/60, 502/64, 68, 208, 214
See application file for complete search history.

(56) References Cited

U.S. PATENT DOCUMENTS

| | | | |
|---|---|---|---|
| 4,062,905 A | 12/1977 | Chang et al. | |
| 4,079,095 A | 3/1978 | Givens et al. | |
| 4,310,440 A | 1/1982 | Wilson et al. | |
| 4,343,723 A | 8/1982 | Rogers et al. | |
| 4,440,871 A | 4/1984 | Lok et al. | |
| 4,443,553 A | 4/1984 | Chiang et al. | |
| 4,499,327 A | 2/1985 | Kaiser | |
| 4,542,118 A | 9/1985 | Nozemack et al. | |
| 4,603,117 A | 7/1986 | Sato et al. | |
| 4,631,261 A | 12/1986 | Sato et al. | |
| 4,645,655 A | 2/1987 | Whittam | |
| 4,677,242 A | 6/1987 | Kaiser | |
| 4,677,243 A | 6/1987 | Kaiser | |
| 4,681,864 A * | 7/1987 | Edwards et al. ............. 502/63 |
| 4,686,316 A * | 8/1987 | Morrison .................... 585/708 |
| 4,814,316 A * | 3/1989 | Pellet et al. ................. 502/214 |
| 4,826,793 A | 5/1989 | Velten et al. | |
| 4,861,743 A | 8/1989 | Flank et al. | |
| 4,861,938 A | 8/1989 | Lewis et al. | |
| 4,873,390 A | 10/1989 | Lewis et al. | |
| 4,952,544 A | 8/1990 | McCauley | |
| 4,970,183 A | 11/1990 | Nakamoto et al. | |
| 4,973,792 A | 11/1990 | Lewis et al. | |
| 4,983,423 A | 1/1991 | Goldsmith | |
| 4,987,110 A | 1/1991 | Scherzer | |
| 5,079,202 A | 1/1992 | Kumar et al. | |
| 5,095,163 A | 3/1992 | Barger | |
| 5,098,685 A | 3/1992 | Casci et al. | |
| 5,110,776 A | 5/1992 | Chitnis et al. | |
| 5,126,298 A | 6/1992 | Absil et al. | |
| 5,126,308 A | 6/1992 | Barger et al. | |
| 5,160,601 A | 11/1992 | Pecoraro | |
| 5,168,084 A | 12/1992 | Peller et al. | |
| 5,194,412 A | 3/1993 | Roberie et al. | |
| 5,248,647 A | 9/1993 | Barger | |
| 5,256,173 A * | 10/1993 | Rastelli ....................... 95/141 |
| 5,286,369 A | 2/1994 | Roberie et al. | |
| 5,298,153 A | 3/1994 | Scherzer | |
| 5,346,875 A | 9/1994 | Wachter et al. | |
| 5,348,643 A | 9/1994 | Absil et al. | |
| 5,365,003 A * | 11/1994 | Chang et al. ............... 585/470 |
| 5,367,100 A | 11/1994 | Gongwei et al. | |
| 5,407,881 A | 4/1995 | Kitamura et al. | |
| 5,434,326 A | 7/1995 | Gajda et al. | |
| 5,456,821 A | 10/1995 | Absil et al. | |
| 5,478,787 A | 12/1995 | Dandekar et al. | |
| 5,516,957 A | 5/1996 | Dandekar et al. | |
| 5,714,662 A | 2/1998 | Vora et al. | |
| 5,807,474 A | 9/1998 | Balai et al. | |

(Continued)

FOREIGN PATENT DOCUMENTS

CN 1060304 4/1992

(Continued)

OTHER PUBLICATIONS

Torsten Maurer et al, *Aggregation and Peptization Behavior of Zeolite Crystals in Sols and Suspensions*, Industrial Engineering Chemical Res. 2001, 40, American Chemical Society, pp. 2573-2579, 2001.

(Continued)

Primary Examiner—David Sample

(57) ABSTRACT

The invention relates to a molecular sieve catalyst composition, to a method of making or forming the molecular sieve catalyst composition, and to a conversion process using the catalyst composition. In particular, the invention is directed to making a formulated molecular sieve catalyst composition from a slurry of formulation composition of a synthesized molecular sieve that has not been fully dried, a binder and an optional matrix material. In a more preferred embodiment, the weight ratio of the binder to the molecular sieve and/or the solid content of the slurry is controlled to provide an improved attrition resistant catalyst composition, particularly useful in a conversion process for producing olefin(s), preferably ethylene and/or propylene, from a feedstock, preferably an oxygenate containing feedstock.

46 Claims, No Drawings

U.S. PATENT DOCUMENTS

| | | | |
|---|---|---|---|
| 5,849,258 A | 12/1998 | Lujano et al. | |
| 5,877,379 A | 3/1999 | Wu et al. | |
| 5,888,378 A | 3/1999 | Kowalski | |
| 5,912,393 A | 6/1999 | Barer et al. | |
| 5,942,104 A | 8/1999 | Miller | |
| 5,961,817 A | 10/1999 | Wachter et al. | |
| 6,022,471 A | 2/2000 | Wachter et al. | |
| 6,049,017 A | 4/2000 | Barger et al. | 585/324 |
| 6,051,745 A | 4/2000 | Wu et al. | |
| 6,111,037 A | 8/2000 | Auburn et al. | |
| 6,114,268 A | 9/2000 | Wu et al. | |
| 6,153,552 A | 11/2000 | Wachter et al. | |
| 6,166,282 A | 12/2000 | Miller | |
| 6,319,393 B1 | 11/2001 | Macedo | |
| 6,329,315 B1 | 12/2001 | Denton et al. | |
| 6,440,894 B1 | 8/2002 | Martens et al. | |
| 6,521,562 B1* | 2/2003 | Clem et al. | 502/214 |
| 6,710,008 B1* | 3/2004 | Chang et al. | 502/214 |
| 2003/0181322 A1* | 9/2003 | Chang et al. | 502/214 |

FOREIGN PATENT DOCUMENTS

| | | |
|---|---|---|
| CN | 1240814 | 1/2000 |
| CN | 1240814 A | 1/2000 |
| CN | 1060304 C | 1/2001 |
| DE | 3602066 | 7/1987 |
| DE | 3602066 A1 | 7/1987 |
| EP | 0178723 | 4/1986 |
| EP | 0236548 | 9/1987 |
| EP | 0273736 | 7/1988 |
| EP | 0325487 | 7/1989 |
| EP | 0 359 841 | 3/1990 |
| EP | 359 843 | 3/1990 |
| EP | 0365336 | 4/1990 |
| EP | 0358261 | 4/1994 |
| EP | 0496226 | 3/1995 |
| EP | 0488690 | 5/1995 |
| EP | 0503876 | 7/1995 |
| EP | 0541101 | 1/1996 |
| EP | 0488427 | 5/1996 |
| EP | 0925831 | 12/1999 |
| EP | 1002577 | 5/2000 |
| EP | 1101735 | 5/2001 |
| EP | 1106576 | 6/2001 |
| EP | 1116775 | 7/2001 |
| GB | 2109696 | 6/1983 |
| GB | 2118063 | 6/1983 |
| JP | 61149244 | 7/1986 |
| JP | 61227843 | 10/1986 |
| JP | 62255440 | 11/1987 |
| JP | 63214354 | 9/1988 |
| JP | 63270545 | 11/1988 |
| JP | 63270546 | 11/1988 |
| JP | 1207138 | 8/1989 |
| JP | 286846 | 3/1990 |
| JP | 2149417 | 6/1990 |
| JP | 2273544 | 11/1990 |
| JP | 02298352 A | 12/1990 |
| JP | 05247474 | 9/1993 |
| JP | 9225305 | 9/1997 |
| JP | 97225305 A | 9/1997 |
| WO | 93/13013 | 7/1993 |
| WO | 99/21651 | 5/1999 |
| WO | 00/06314 | 2/2000 |
| WO | 92/02299 | 5/2001 |
| WO | 01/96106 | 12/2001 |
| WO | 02/05952 | 1/2002 |
| WO | WO 02/05950 | 1/2002 |
| WO | WO 99/21651 | 5/2006 |

OTHER PUBLICATIONS

Valeria Tohver et al. *Nanoparticle Engineering of Complex Fluid Behavior, Langmuir 2001*, 17, pp. 8414-8421, 2001.

Mark C. Lotallo et al, *Nanocrystalline Zeolites, Synthesis, Characterization, and Applications with Emphasis on Zeolite & Nanoclusters, Advanced Catalysts and Nanostructured Materials; Modern Synthetic Methods*, Academic Press, pp. 307-343, no date.

Perry, Robert et al.; "Chemical Engineers' Handbook Fifth Edition," McGraw-Hill Book Company, pp. 19-57 - 19-100, 1973.

Olphen H. van; "Clay Colloid Chemisrty For Clay Technologists, Geologists, and Soil Scientists," Kreiger Publishing Company, p. 4, 1963.

Woltermann G.M, et al.; "Commercial Preparation and Characterization of FCC Catalysts," Fluid Catalytic Cracking: Science and Technology, Studies in Surface Science and Catalysis, vol. 76, pp. 105-144, 1993.

Gwyn, J. E.; "On the Particle Size Distribution Function and he Attrition of Cracking Catalysts," AIChE Journal, vol. 15, No. 1, pp. 35-39, 1969.

Hsu, W. et al.; "Preparation and Properties of Monodispersed Colloidal Particles of Lanthanide Compounds. 2. Cerium(IV)," Langmuir, vol. 4, pp.31-37, 1988.

Garg, A. et al.; "Preparation and Properties of Uniformly Coated Inorganic Colloidal Particles. 2. Chromium Hydrous Oxide on Hematite, " Langmuir, vol. 4, pp. 38-44, 1988.

Otterstedt J. et al.; "Small Particles Technology," Plenum Press, New York and London, vol. 6 pp. 258-260, 1998.

Tadros Th.F.; "Solid/Liquid Dispersions," Academic Press Inc (London), vol. 1, pp. 1-16, 1987.

Lyklema J.; "Structure of the solid/liquid interface and the electrical double layer," Academic Press Inc (London), vol. 3, pp. 63-90, 1987.

Akporiaye, D.E. et al.; "The synthesis and characterization of SAPO-43," Zeolites, vol. 17, pp. 517-522, 1996.

* cited by examiner

MOLECULAR SIEVE CATALYST COMPOSITION, ITS MAKING AND USE IN CONVERSION PROCESSES

This application claims the benefit of Provisional Application No. 60/302,462, filed Jul. 2, 2001.

FIELD OF THE INVENTION

The present invention relates to a molecular sieve catalyst composition, to a method of making or forming the molecular sieve catalyst composition, and to a conversion process using the catalyst composition.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred methanol conversion process is generally referred to as a methanol-to-olefin(s) process, where methanol is converted to primarily ethylene and/or propylene in the presence of a molecular sieve.

Molecular sieves are porous solids having pores of different sizes such as zeolites or zeolite-type molecular sieves, carbons and oxides. The most commercially useful molecular sieves for the petroleum and petrochemical industries are known as zeolites, for example aluminosilicate molecular sieves. Zeolites in general have a one-, two- or three-dimensional crystalline pore structure having uniformly sized pores of molecular dimensions that selectively adsorb molecules that can enter the pores, and exclude those molecules that are too large.

There are many different types of molecular sieves well known to convert a feedstock, especially an oxygenate containing feedstock, into one or more olefin(s). For example, U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphates, often represented by ALPO$_4$.

One of the most useful molecular sieves for converting methanol to olefin(s) is a silicoaluminophosphate molecular sieves. Silicoaluminophosphate (SAPO) molecular sieves contain a three-dimensional microporous crystalline framework structure of [SiO$_2$], [AlO$_2$] and [PO$_2$] corner sharing tetrahedral units. SAPO synthesis is described in U.S. Pat. No. 4,440,871, which is herein fully incorporated by reference. SAPO is generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, is shown in U.S. Pat. Nos. 4,499,327, 4,677,242, 4,677,243, 4,873,390, 5,095,163, 5,714,662 and 6,166,282, all of which are herein fully incorporated by reference.

Typically, molecular sieves are formed into molecular sieve catalyst compositions to improve their durability in commercial conversion processes. The collisions within a commercial process between catalyst composition particles themselves, the reactor walls, and other reactor systems cause the particles to breakdown into smaller particles called fines. The physical breakdown of the molecular sieve catalyst composition particles is known as attrition. Fines often exit the reactor in the effluent stream resulting in problems in recovery systems. Catalyst compositions having a higher resistance to attrition generate fewer fines, less catalyst composition is required for conversion, and longer life times result in lower operating costs.

Molecular sieve catalyst compositions are formed by combining a molecular sieve and a matrix material usually in the presence of a binder. The purpose of the binder is hold the matrix material, often a clay, to the molecular sieve. The use of binders and matrix materials in the formation of molecular sieve catalyst compositions is well known for a variety of commercial processes. It is also known that the way in which the molecular sieve catalyst composition is made or formulated affects catalyst composition attrition.

Example of methods of making catalyst compositions include: U.S. Pat. No. 5,126,298 discusses a method for making a cracking catalyst having high attrition resistance by combining two different clay particles in separate slurries with a zeolite slurry and a source of phosphorous, and spray drying a mixture of the slurries having a pH below 3; U.S. Pat. No. 4,987,110 and 5,298,153 relates to a catalytic cracking process using a spray dried attrition resistant catalyst containing greater than 25 weight percent molecular sieve dispersed in a clay matrix with a synthetic silica-alumina component; U.S. Pat. Nos. 5,194,412 and 5,286,369 discloses forming a catalytic cracking catalyst of a molecular sieve and a crystalline aluminum phosphate binder having a surface area less than 20 m$^2$/g and a total pore volume less than 0.1 cc/g; U.S. Pat. No. 4,542,118 relates to forming a particulate inorganic oxide composite of a zeolite and aluminum chlorhydrol that is reacted with ammonia to form a cohesive binder; U.S. Pat. No. 6,153,552 claims a method of making a catalyst, by drying a slurry of a SAPO molecular sieve, an inorganic oxide sol, and an external phosphorous source; U.S. Pat. No. 5,110,776 illustrates the formation of a zeolite containing catalytic catalyst by modifying the zeolite with a phosphate containing solution; U.S. Pat. No. 5,348,643 relates to spray drying a zeolite slurry with a clay and source of phosphorous at a pH of below 3; U.S. patent Ser. No. 4,973,792 is directed to a conversion process using a formulated molecular sieve catalyst composition, however, there is no mention of the solid content of the slurry spray dried, nor any discussion of the amount of liquid medium in the SAPO-34 added to the slurry; U.S. patent application Ser. No. 09/891,674 filed Jun. 25, 2001 discusses a method for steaming a molecular sieve to remove halogen; U.S. Pat. No. 5,248,647 illustrates spray drying a SAPO-34 molecular sieve admixed with kaolin and a silica sol; U.S. Pat. No. 5,346,875 discloses a method for making a catalytic cracking catalyst by matching the isoelectric point of each component of the framework structure to the pH of the inorganic oxide sol; Mäurer, et al, *Aggregation and Peptization Behavior of Zeolite Crystals in Sols and Suspensions*, Ind. Eng. Chem. Vol. 40, pages 2573–2579, 2001 discusses zeolite aggregation at or near the isoelectric point; PCT Publication WO 99/21651 describes making a catalyst by drying a mixture of an alumina sol and a SAPO molecular sieve; PCT Publication WO 02/05950 describes making a catalyst composition of a molecular sieve containing attrition particles with fresh molecular sieve; and WO 02/05952 discloses a crystalline metalloaluminophosphate molecular sieve and a matrix material of an inorganic oxide binder and filler where the molecular sieve is present in an amount less than 40 weight percent relative to the catalyst weight and a preferable weight ratio of the binder to molecular sieve close to 1.

Although these molecular sieve catalyst compositions described above are useful in hydrocarbon conversion processes, it would be desirable to have an improved molecular sieve catalyst composition having better attrition resistance and commercially desirable operability and cost advantages.

SUMMARY OF THE INVENTION

This invention provides for a method of making or formulating a molecular sieve catalyst composition and to its use in a conversion process for converting a feedstock into one or more olefin(s).

In one embodiment the invention is directed to a method for formulating a molecular sieve catalyst composition, the method comprising the steps of: (a) providing a synthesized molecular sieve having not been fully dried, or alternatively, partially dried; (b) making a slurry of the synthesized molecular sieve, a binder, and optionally a matrix material; and (c) forming the slurry to produce a formulated molecular sieve catalyst composition. In a preferred embodiment, the synthesized molecular sieve is synthesized from the combination of at least two of the group consisting of a silicon source, a phosphorous source and an aluminum source, optionally in the presence of a templating agent. In a most preferred embodiment, the slurry in step (c) is formed by spray drying. In another preferred embodiment, the weight ratio of binder to molecular sieve in the slurry in step (c) is greater than 0.12 to about 0.45. In yet another embodiment, the slurry contains a solid content of from about 20 percent to about 80 percent based on the total weight of the solids in the slurry on a calcined basis. The solids include the molecular sieve, the binder, and optionally the matrix material. In still another embodiment of any of the above, after step (b) and prior to step (c) the slurry is mixed until 90 percent by volume of the slurry contains particles having a diameter less than 20 μm, preferably less than 10 μm.

In an embodiment, the invention is directed to a method for formulating a molecular sieve catalyst composition, the method comprising the steps of: (a) providing a synthesized molecular sieve in the presence of a first liquid medium; (b) introducing a binder, and optionally adding a second liquid medium and/or a matrix material to form a slurry; and (c) mixing and forming the slurry to produce a formulated molecular sieve catalyst composition, wherein the synthesized molecular sieve is not fully dried or partially dried prior to step (a). In a preferred embodiment, the first and second liquid medium is water, and the amount of the first liquid medium prior to drying is in the range of from 20 weight percent to 70 weight percent based on the total weight of the molecular sieve and first liquid medium. Preferably the synthesized molecular sieve is a silicoaluminophosphate, an aluminophosphate and/or a chabazite (CHA) framework-type molecular sieve. In yet another embodiment, the weight ratio of the binder to the molecular sieve is greater than 0.12 to less than 0.45, wherein the binder is an alumina and the molecular sieve is a silicoaluminophosphate. In yet another embodiment, the slurry contains a solid content of from about 30 percent to about 50 percent, preferably about 35 percent to about 50 percent, and more preferably from about 40 to about 50 percent, based on the total weight of the solids in the slurry on a calcined basis. In still yet another embodiment of any of the above, the slurry is mixed until at least 90 percent by volume of solid particles in the slurry have a diameter less than 20 μm, preferably less than 10 μm.

In another preferred embodiment, the invention relates to a method for making a formulated molecular sieve catalyst composition, the method comprising the steps of: (a) synthesizing with a liquid medium a molecular sieve from the combination of at least two of the group consisting of a silicon source, a phosphorous source and an aluminum source, optionally in the presence of a templating agent, to form a slurry; (b) removing the molecular sieve from the slurry; (c) drying the molecular sieve to a level in the range of from 20 weight percent to 80 weight percent liquid medium based on the total weight of the liquid medium and the molecular sieve; (d) combining the molecular sieve with a binder, and optionally adding the same or different liquid medium and/or with a matrix material, to form a formulation composition; and (e) drying and/or forming the formulation composition to form the formulated molecular sieve catalyst composition. In a preferred embodiment, in step (c) the slurry is dried to a level in the range of from 30 weight percent to 70 weight percent liquid medium, preferably water, based on the total weight of the liquid medium, preferably water, and the molecular sieve. In another embodiment, in step (e) the formulation composition is formed by spray drying the formulation composition to form the formulated molecular sieve catalyst composition. In a further embodiment, prior to step(c) and/or (e), the slurry and/or the formulation composition is washed in a liquid, preferably the liquid is the same as the liquid medium, and most preferably the liquid is water. In another preferred embodiment, the method further comprises a step (f) in which the formulated molecular sieve catalyst composition is calcined. In another embodiment, the weight ratio of the binder to the molecular sieve is in the range of greater than 0.1 to less than 0.5, preferably in the range greater than 0.12 to 0.45, and most preferably in the range of from 0.13 to about 0.40. In yet another embodiment of any of the above, slurry contains a solid content of from about 35 percent to about 50 percent based on the total weight of the solids in the slurry on a calcined basis. In still another embodiment of any of the above, the combining of the slurry comprises the step of mixing the slurry comprising a liquid and solid particles until at least 90 percent by volume of the solid particles have a diameter less than 20 μm, preferably less than 10 μm.

In yet another embodiment, the invention is directed to a process for producing olefin(s) in the presence of any of the above formulated molecular sieve catalyst compositions. In particular, the process involves producing olefin(s) in a process for converting a feedstock, preferably a feedstock containing an oxygenate, more preferably a feedstock containing an alcohol, and most preferably a feedstock containing methanol in the presence of one or more of the formulated molecular sieve catalyst compositions discussed above.

DETAILED DESCRIPTION OF THE INVENTION

Introduction

The invention is directed toward a molecular sieve catalyst composition, its making, and to its use in the conversion of a hydrocarbon feedstock into one or more olefin(s). The molecular sieve catalyst composition is made or formed from the combination of a molecular sieve, a binder, and optionally, most preferably, a matrix material. Typically in the art a dried or calcined molecular sieve is combined with a binder and/or matrix material. However, it has been surprisingly found that using a molecular sieve that has not been fully dried that is combined with a binder and/or a matrix material an improved formulated molecular sieve catalyst composition is made. In particular, using a partially dried molecular sieve with a binder and/or a matrix material results in making a formulated molecular sieve catalyst composition having improved resistance to attrition. This results in an improved catalyst composition more resistant to breaking apart in a conversion processes, and therefore having an extended catalyst life. Additionally, not calcining the molecular sieve after its synthesis also reduces the cost associated with the synthesis and also improves its susceptibility to deactivation especially in its storage or transportation.

It has been known in the art that varying the weight percent of the molecular sieve in the total catalyst composition is important. However, it has also been surprisingly found that the weight ratio of the binder to the molecular sieve, especially where the molecular sieve is partially dried as discussed above, is important to making or forming an attrition resistance catalyst composition. Without being bound to any particular theory it is believed that when the weight ratio of the binder to molecular sieve is too high then the surface area of the catalyst composition decreases resulting in lower conversion rates, and when the weight ratio of the binder to molecular sieve is too low then the catalyst composition will break apart into fines more easily.

It has also been discovered that in addition to the dryness of the molecular sieve and the binder to molecular sieve ratio in the formulation of a molecular sieve catalyst composition, that the amount of solids present in a slurry of the molecular sieve and the binder, optionally including a matrix material, used in a spray drying process for example is important. When the solids content of the slurry is too low or too high the attrition resistance properties of the molecular sieve catalyst composition is reduced. The amount of solids in combination with the other discoveries discussed above also determines the level of attrition resistance a particular molecular sieve catalyst composition has.

Molecular Sieves and Catalysts Thereof

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI framework-type or a CHA framework-type, or a combination thereof, most preferably a CHA framework-type.

Molecular sieve materials all have 3-dimensional framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves are described in R. Szostak, *Handbook of Molecular Sieves*, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

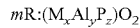

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of M, Al and P as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the ratio of CHA to AEI is greater than 1:1.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline molecular sieve material is formed, and then recovered by filtration, centrifugation and/or decanting.

For purposes of this patent application and appended claims, the term "not being fully dried" is defined to include no drying up to not calcining the crystalline molecular sieve material or the synthesized molecular sieve.

For purposes of this patent application and appended claims, the term "partially dried" is defined to include drying the crystalline molecular sieve material or the synthesized molecular sieve to a level wherein after drying the amount of templating agent with the crystalline molecular sieve material or the synthesized molecular sieve is in the range of from about 50 weight percent, preferably about 60 weight percent, more preferably about 70 weight percent, and most preferably about 80 percent to 100 weight percent of the original amount of templating agent used to form the crystalline molecular sieve material or the synthesized molecular sieve originally.

In another preferred embodiment, the crystalline molecular sieve material or synthesized molecular sieve is wet, preferably with water, when used in the formulation of a molecular sieve catalyst composition and is termed a "wet filtercake".

In one particular embodiment, the crystalline molecular sieve material or the synthesized molecular sieve is optionally dried, preferably in air, to a level such that the synthesized molecular sieve has in the range of from about 0 weight percent to about 80 weight percent liquid, preferably where the liquid is water, based on the total weight of the synthesized molecular sieve and liquid, preferably the range is from greater than 5 weight percent to about 70 weight percent, more preferably from about 10 weight percent to about 70 weight percent, and most preferably from about 20 weight percent to about 60 weight percent.

Determination of the percentage of liquid or liquid medium and the percentage of template for purposes of this patent specification and appended claims uses a Thermal Gravimetric Analysis (TGA) technique as follows: An amount a SAPO-34 molecular sieve material, the sample, is loaded into a sample pan of a Cahn TG-121 Microbalance, available from Cahn Instrument, Inc., Cerritos, Calif. During the TGA technique, a flow of 114 cc/min (STP) air was used. The sample is then heated from 25° C. to 180° C. at 30° C./min, held at 180° C. for 3 hours or until the weight of this sample becomes constant. The weight loss the percentage to the starting SAPO-34 molecular sieve material is then treated as the percentage of the liquid or liquid medium. Subsequently, the sample is heated at 30° C./min from 180° C. to 650° C. and held at 650° C. for 2 hours. This weight loss as a percentage of the original sample weight during this treatment is regarded as the weight loss of the templating agent. The total weight loss as a percentage in terms of the original first sample weight during this entire TGA treatment is defined as Loss-On-Ignition (LOI).

In a preferred embodiment, the crystalline molecular sieve or synthesized molecular sieve is used directly without dehydration after synthesis, and then forming the slurry of the crystalline molecular sieve or synthesized molecular sieve, binder, and optional matrix material, and then formulate the slurry into the molecular sieve catalyst composition of the invention.

In a preferred embodiment the molecular sieves are synthesized by forming a reaction product of a source of silicon, a source of aluminum, a source of phosphorous, an organic templating agent, preferably a nitrogen containing organic templating agent. This particularly preferred embodiment results in the synthesis of a silicoaluminophosphate crystalline material that is then isolated by filtration, centrifugation and/or decanting.

Non-limiting examples of silicon sources include silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butyl-amine, ethylenediamine, pyrrolidine, polyethylenimine and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source.

A synthesis mixture containing at a minimum a silicon-, aluminum-, and/or phosphorous-composition, and a templating agent, should have a pH in the range of from 2 to 10, preferably in the range of from 4 to 9, and most preferably in the range of from 5 to 8. Generally, the synthesis mixture is sealed in a vessel and heated, preferably under autogenous pressure, to a temperature in the range of from about 80° C. to about 250° C., and more preferably from about 150° C. to about 180° C. The time required to form the crystalline product is typically from immediately up to several weeks, the duration of which is usually dependent on the temperature; the higher the temperature the shorter the duration. Typically, the crystalline molecular sieve product is formed, usually in a slurry state, and is recovered by any standard technique well known in the art, for example centrifugation or filtration.

In a preferred embodiment, the isolated or separated crystalline product, the synthesized molecular sieve, is washed, typically using a liquid such as water, from one to many times, or in a semi-continuous or continuous way for variable lengths of time. The washed crystalline product is then optionally dried, preferably in air to a level such that the crystalline product or synthesized molecular sieve has in the range of from about 0 weight percent to about 80 weight percent liquid, preferably were the liquid is water, based on the total weight of the crystalline product or synthesized molecular sieve and liquid medium, preferably the range is from about greater than 1 weight percent to about 80 weight percent, more preferably from about 10 weight percent to about 70 weight percent, even more preferably from about 20 to about 60 weight percent, and most preferably from about 40 weight percent to about 60 weight percent. This liquid containing crystalline product, synthesized molecular sieve or wet filtercake, is then used below in the formulation of the molecular sieve catalyst composition of the invention.

In one embodiment, where the synthesized molecular sieve is partially dried, for example by heating, the temperature and time period is sufficient to maintain a major of the templating agent, where more than 50% of the templating agent is retained. In addition a preferred temperature for heating the synthesized molecular sieve is typically about 180° C., preferably less than 150° C., even more preferably less than 120° C. for about 3 hours or less.

Molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

Method for Making Molecular Sieve Catalyst Compositions

Once the molecular sieve is synthesized as described above, depending on the requirements of the particular conversion process, the molecular sieve is then formulated into a molecular sieve catalyst composition, particularly for commercial use. The molecular sieves synthesized above are made or formulated into molecular sieve catalyst compositions by combining the synthesized molecular sieve(s) with a binder and optionally, but preferably, a matrix material to form a formulation composition. This formulation composition is formed into useful shape and sized particles by well-known techniques such as spray drying, pelletizing, extrusion, and the like, spray drying being the most preferred. It is also preferred that after spray drying for example that the formulation composition is then calcined.

In one embodiment, the weight ratio of the binder to the molecular sieve is in the range of from about 0.1 to 0.5, preferably in the range of from 0.1 to less than 0.5, more preferably in the range of from 0.11 to 0.48, even more preferably from 0.12 to about 0.45, yet even more preferably from 0.13 to less than 0.45, and most preferably in the range of from 0.15 to about 0.4. In another embodiment, the weight ratio of the binder to the molecular sieve is in the range of from 0.11 to 0.45, preferably in the range of from about 0.12 to less than 0.40, more preferably in the range of from 0.15 to about 0.35, and most preferably in the range of from 0.2 to about 0.3. All values between these ranges are included in this patent specification.

In another embodiment, the molecular sieve catalyst composition or formulated molecular sieve catalyst composition has a micropore surface area (MSA) measured in $m^2$/g-molecular sieve that is about 70 percent, preferably about 75 percent, more preferably 80 percent, even more preferably 85 percent, and most preferably about 90 percent of the MSA of the molecular sieve itself. The term "MSA on a contained sieve basis of the molecular sieve by itself" or the term "MSA of X $m^2$/g-molecular sieve" means that the calculated MSA of a molecular sieve catalyst composite is the measured MSA divided by the contained fraction of the molecular sieve. For example, a molecular sieve catalyst composite with a measured MSA of 200 $m^2$/g and containing 40% molecular sieve would be calculated to have an "MSA on a contained sieve basis of the molecular sieve by itself" of 200 $m^2$/g/0.4=500 $m^2$/g-contained molecular sieve.

In one embodiment, the catalyst composition has a MSA on a contained molecular sieve basis of the molecular sieve by itself in the range of from 400 $m^2$/g-molecular sieve to about 600 $m^2$/g-molecular sieve, preferably an MSA in the range of from 425 $m^2$/g-molecular sieve to about 575 $m^2$/g-molecular, more preferably in the range of from 425 $m^2$/g-molecular sieve to about 550 $m^2$/g-molecular sieve, and most preferably in the range of from about 450 $m^2$/g-molecular sieve to about 550 $m^2$/g-molecular sieve.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrate, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol AL20DW, available from Nyacol Nano Technologies, Inc., Ashland, Mass.

The synthesized molecular sieves described above, in a preferred embodiment, is combined with a binder and one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a $d_{90}$ particle size distribution of less than about 1 µm.

In one embodiment, the binder, the synthesized molecular sieve and the matrix material are combined in the presence of a liquid such as water to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid.

Upon combining the synthesized molecular sieve and the matrix material, optionally with a binder, in a liquid to form a slurry, mixing, preferably rigorous mixing is needed to produce a substantially homogeneous mixture containing the synthesized molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The liquid containing synthesized molecular sieve and matrix material, and the optional binder, are in the same or different liquid, and are combined in any order, together, simultaneously, sequentially, or a combination thereof. In the preferred embodiment, the same liquid, preferably water is used.

The molecular sieve catalyst composition in a preferred embodiment is made by preparing a slurry containing a molecular sieve, a binder, and, optionally while preferably, a matrix material. The solids content of the preferred slurry includes about 20% to about 50% by weight of the molecular sieve, preferably from about 30% to about 48% by weight of the molecular sieve, more preferably from about 40% to about 48% by weight molecular sieve, about 5% to about 20%, preferably from about 8% to about 15%, by weight of the binder, and about 30% to about 80%, preferably about 40% to about 60%, by weight of the matrix material.

In another most preferred embodiment, the solids content in a slurry comprising a molecular sieve, a binder, and optionally a matrix material, and a liquid medium is in the range of from about 20 weight percent to about 80 weight percent, more preferably in the range of from 30 weight percent to about 70 weight percent, even more preferably in the range of from 35 weight percent to 60 weight percent, still even more preferably from about 36 weight percent to about 50 weight percent, yet even more preferably in the range of from 37 weight percent to about 45 weight percent, and most preferably in the range of from 38 weight percent to about 42 weight percent.

As the slurry is mixed, the solids in the slurry aggregate preferably to a point where the slurry contains solid molecular sieve catalyst composition particles. It is preferable that these particles are small and have a uniform size distribution such that the $d_{90}$ diameter of these particles is less than 20 µm, more preferably less than 15 µm, and most preferably less than 10 µm. The $d_{90}$ for purposes of this patent application and appended claims means that 90 percent by volume of the particles in the slurry have a particle diameter lower than the $d_{90}$ value. For the purposes of this definition, the particle size distribution used to define the $D_{90}$ is measured using well known laser scattering techniques using a Honeywell (Microtrac Model 3000 particle size analyzer from Microtrac, Inc., Clearwater, Fla.). In one embodiment, the slurry of the invention contains at least 90 percent by volume of the molecular sieve catalyst composition particles comprising the molecular sieve, binder, and optional matrix material, have a diameter of less than 20 µm, preferably less than 15 µm, and most preferably less than 10 µm.

In one preferred embodiment the slurry comprising a liquid portion and solid portion, wherein the solid portion comprises solid particles, the solid particles comprising a molecular sieve, a binder and/or a matrix material; wherein the slurry contains in the range of from about 30 weight percent to about 50 weight percent solid particles, preferably from about 35 weight percent to 45 weight percent, and at least 90 percent of the solid particles having a diameter less than 20 µm, preferably less than 10 µm.

The molecular sieve catalyst composition particles contains some water, templating agent or other liquid components, therefore, the weight percents that describe the solid content in the slurry are preferably measured, preferably exclusive of the amount of water, templating agent and/or other liquid contained within the particle. In the most preferred condition for measuring solids content is on a calcined basis. Thus, the weight of the solid content in the slurry is equal to or very similar to the weight of the calcined molecular sieve catalyst composition. On a calcined basis, the solid content in the slurry, more specifically, the molecular sieve catalyst composition particles in the slurry, are from about 20% to 45% by weight molecular sieve, 5% to 20% by weight binder, and from about 30% to 80% by weight matrix material.

In one embodiment, the slurry of the synthesized molecular sieve, binder and matrix material is mixed or milled to achieve a sufficiently uniform slurry of sub-particles of the molecular sieve catalyst composition to form a formulation composition that is then fed to a forming unit that produces the molecular sieve catalyst composition or formulated molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, any one or a combination of the slurries described above, more particularly a slurry of the synthesized molecular sieve, matrix material, and binder, is co-fed to the spray dryer with a drying gas with an average inlet temperature ranging from 200° C. to 550° C., and a combined outlet temperature ranging from 100° C. to about 225° C. In an embodiment, the average diameter of the spray dried formed catalyst composition is from about 40 µm to about 300 µm, preferably from about 50 µm to about 250 µm, more preferably from about 50 µm to about 200 µm, and most preferably from about 65 µm to about 90 µm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve composition in a powder or a microsphere form.

Generally, the size of the microspheres is controlled to some extent by the solids content of the slurry. However, control of the size of the catalyst composition and its spherical characteristics are controllable by varying the slurry feed properties and conditions of atomization.

Other methods for forming a molecular sieve catalyst composition is described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, preferably from about 10% to about 90%, more preferably from about 10% to about 80%, even more preferably from about 20% to about 70%, and most preferably from about 25% to about 60% by weight of the molecular sieve based on the total weight of the molecular sieve catalyst composition.

Once the molecular sieve catalyst composition is formed in a substantially dry or dried state, to further harden and/or activate the formed catalyst composition, a heat treatment such as calcination, at an elevated temperature is preferably performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof. In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 20 hours. In a preferred embodiment, the molecular sieve catalyst composition is heated in nitrogen at a temperature of from about 600° C. to about 700° C. Heating is carried out for a period of time typically from 15 minutes to 15 hours, preferably from 30 minutes to about 10 hours, more preferably from about 30 minutes to about 5 hours.

In one embodiment, the attrition resistance of a molecular sieve catalyst composition is measured using an Attrition Rate Index (ARI), measured in weight percent catalyst composition attrited per hour. ARI is measured by adding 6.0 g of catalyst composition having a particles size ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in weight percent per hour (wt. %/hr). ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

In one embodiment, the molecular sieve catalyst composition or formulated molecular sieve catalyst composition has an ARI less than 15 weight percent per hour, preferably less than 10 weight percent per hour, more preferably less than 5 weight percent per hour, and even more preferably less than 2 weight percent per hour, and most preferably less than 1 weight percent per hour. In one embodiment, the molecular sieve catalyst composition or formulated molecular sieve catalyst composition has an ARI in the range of from 0 weight percent per hour to less than 5 weight percent per hour, more preferably from about 0.05 weight percent per hour to less than 3 weight percent per hour, and most preferably from about 0.01 weight percent per hour to less than 2 weight percent per hour.

In one preferred embodiment of the invention, the molecular sieve catalyst composition or formulated molecular sieve catalyst composition comprises a synthesized molecular sieve in an amount of from 20 weight percent to 60 weight percent, a binder in an amount of from 5 to 50 weight percent, and a matrix material in an amount of from 0 to 78 weight percent based on the total weight of the catalyst composition, upon calcination, and the catalyst composition having weight ratio of binder to sieve of from 0.1 to less than 0.5. In addition, the catalyst composition of this embodiment has an MSA on a contained sieve basis of the molecular sieve by itself from 450 $m^2$/g-molecular sieve to 550 $m^2$/g-molecular sieve, and/or an ARI less than 2 weight percent per hour.

Process for Using the Molecular Sieve Catalyst Compositions

The molecular sieve catalyst compositions or formulated molecular sieve catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene. Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, methanol-to-olefins (MTO). In a GTO process, typically natural gas is converted into a synthesis gas that is converted into an oxygenated feedstock, preferably containing methanol, where the oxygenated feedstock is converted in the presence of a molecular sieve catalyst composition into one or more olefin(s), preferably ethylene and/or propylene. In a MTO process, typically an oxygenated feedstock, most preferably a methanol containing feedstock, is converted in the presence of a molecular sieve catalyst composition thereof into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25.

In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar or the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor. Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference. In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference. Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference. In yet another embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system, a complete regeneration. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference. In another embodiment, the optimum level of coke on the molecular sieve catalyst composition in the reaction zone is maintained by controlling the flow rate of oxygen containing gas flowing to the regenerator, a partial regeneration. Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and/or regenerated molecular sieve catalyst composition and/or cooled regenerated molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated and fresh molecular sieve catalyst composition that have varying levels of carbon and carbon-like deposits, coke. The measured level of these deposits, specifically coke, represents an average of the levels on individual molecular sieve catalyst composition particles.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants. Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology, 4th Edition*, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In one embodiment, the effluent gas withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water.

Suitable well known reaction systems as part of the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel. Non-limiting examples of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin. In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

EXAMPLES

In order to provide a better understanding of the present invention including representative advantages thereof, the following examples are offered.

Constituents of a mixture used for formulating catalysts will generally contain volatile components, including, but not limited to, water and, in the case of molecular sieve, organic template. It is common practice to describe the amount or proportion of these constituents as being on a "calcined basis". Calcination involves heating a material in the presence of air at an elevated temperature sufficient to dry and remove any contained volatile, combustible or pyrolizable content (650° C. for one or more hours). On a "calcined basis" is defined, for the purposes of the current invention, as the amount or fraction of each component remaining after it has been mathematically reduced to account for losses in weight expected to occur if the component had been calcined. Thus, 10 grams of a component containing 25% template would be described as "7.5 g on a calcined basis". Synthesis of a SAPO-34 molecular sieve is well known, and in the Examples below has a MSA of about 450 $m^2/g$ to 550 $m^2/g$-molecular sieve.

Micropore surface area (MSA) is a measurement of the amount of micropores present in a porous material. MSA is the difference between the total surface area-BET surface area determined from relative pressures that gives a linear plot and the external surface area, calculated from the slope of the linear region of the t-plot with a small correction to put it on the same basis as the BET surface area. This approach has been used for determining the amount of zeolite in cracking catalysts by Johnson [M. F. L. Johnson, J. Catal., 52, 425–431 (1978)]. The t-plot is a transformation of the adsorption isotherm in which relative pressure is replaced by t, the statistical thickness of the adsorbed layer on nonporous material at the corresponding relative pressure; see Lippens and de Boer for determining various characteristics of pores systems, such as pore shapes [B. C. Loppens, and J. H. de Boer, J. Catal., 4, 319 (1965)]. Sing [K. S. W. Sing, Chem. Ind., 829 (1967)] has introduced that the extrapolation of a linear t-plot to t=0 can yield the volume of micropores.

MSA is determined using a MICROMERITICS Gemini 2375 from Micromeritics Instrument Corporation, Norcross, Ga. is used. An amount, 0.15 g to 0.6 g, of the sample was loaded into the sample cell for degassing at 300° C. for a minimum of 2 hours. During the analysis, the Evacuation Time is 1.0 minute, no free space is used, and sample Density of 1.0 g/cc is used. Thirteen (13) adsorption data points are collected with adsorption targets of:

| Data Point | Adsorption Target ($p/p_o$) | Data Point | Adsorption Target ($p/p_o$) |
| --- | --- | --- | --- |
| 1 | 0.00500 | 8 | 0.25000 |
| 2 | 0.07500 | 9 | 0.30000 |
| 3 | 0.01000 | 10 | 0.40000 |
| 4 | 0.05000 | 11 | 0.60000 |

-continued

| Data Point | Adsorption Target (p/p$_o$) | Data Point | Adsorption Target (p/p$_o$) |
|---|---|---|---|
| 5 | 0.10000 | 12 | 0.75000 |
| 6 | 0.15000 | 13 | 0.95000 |
| 7 | 0.20000 | | |

The correction factor used in the t-plot is 0.975. No desorption points are collected. Other analysis parameters include, Analysis Mode: Equilibrate; Equilibration Time: 5 second; Scan Rate: 10 seconds. A t-plot from 0.00000 to 0.90000 is constructed using the ASTM certified form of the Harkins and Jura equation (H-J Model): $t(p)=(13.99/(0.034-\log(p/p_o)))0.5$. It is shown by Cape and Kibby [J. A. Cape and C. L. Kibby, J. Colloids and Interface Science, 138, 516–520 (1990)] that the conventional BET surface area of a microporous material can be decomposed quantitatively into the external area and the micropore volume, as expressed by equation given below: $S_{micro}=S_{tot}-S_{ext}=v_m/d_j$, where $v_m$ is the micropore volume, $S_{mciro}$ is the micropore area calculated from $S_{tot}$ and $S_{ext}$. $S_{tot}$ is given by the conventional BET method, and $S_{ext}$ is the external area taken from the t-plot. $d_j$ is a nonphysical length the value of which depends on the pressure used in the experiments. The proportionality factor, $d_j$, is determined quantitatively by the pressures used in the BET fits.

Example 1

The SAPO-34 molecular sieve used in the following example that has not been fully dried and has not been calcined was recovered from a hydrothermal synthesis well known in the art. A slurry containing 45 wt % solid (on a calcined basis), 40% being SAPO-34 molecular sieve that has not been completely dried or calcined, 10.6% $Al_2O_3$ (alumina sol, the binder), and 49.4% clay (the matrix material), was prepared according to procedure: (A) add 2988.93 g of a SAPO-34 molecular sieve wet filtercake (on a calcined basis of 1621.29 g) (liquid medium content 34.68 weight percent based on the total weight of the molecular sieve and the liquid medium) to 1703.84 g of deionized water, and mixed at 1500 RPM using a Yamato 4000D mixer (Yamato Scientific America Inc., Orangeburg, N.Y.) for 15 minutes, and then followed by a high-shear treatment using the Silverson high shear mixer L4RT-A at 6000 RPM for 10 minutes. This slurry had a pH value of 6.3 measured at 26° C. (B) ACH-Solution: add 869.03 g (on a calcined basis of 429.64 g) of Reheis MicroDry aluminum chlorohydrate (Reheis Inc., Berkeley Heights, N.J.) to 859.12 g of deionized water and mixed at 1500 RPM using a Yamato 4000D mixer (Yamato Scientific America Inc., Orangeburg, N.Y.) for 15 minutes followed by a high-shear treatment using the Silverson high shear mixer at 6000 RPM for 10 minutes. This solution had a pH of 3.3 measured at 31° C. (C) the above SAPO-34 molecular sieve slurry (A) and aluminum chlorohydrate solution (B) were combined and mixed at 1500 RPM using a Yamato 4000D mixer (Yamato Scientific America Inc., Orangeburg, N.Y.) for 15 minutes, and then mixed using the Silverson high-shear mixer at 6000 RPM for 10 minutes. This slurry had a pH value of 4.2 measured at 30° C. (D) add 2302.3 g (on a calcined basis of 2002.30 g) of Engelhard's ASP Ultrafine kaolin clay (Engelhard Corporation, Iselin, N.J.) to the above slurry containing SAPO-34 molecular sieve and aluminum chlorohydrate under constant mixing at 250 to 400 RPM, and then mixed at 1500 RPM using a Yamato 4000D mixer (Yamato Scientific America Inc., Orangeburg, N.Y.) for 15 minutes followed by a high-shear mixing step using the Silverson mixer at 6000 RPM for 10 minutes. (E) the solid content of the slurry was adjusted to contain 45% solids, an amount of 283.97 g of deionized water was added to the above slurry containing SAPO-34 molecular sieve, ACH (the binder), and kaolin clay (the matrix material) followed with 1500 RPM treatment for 15 minutes using the Yamato mixer and subsequent high-shear mixing using the Silverson mixer at 6000 RPM for 10 minutes. This final slurry had a pH value of 3.8 measured at 36° C. This led to 8000 g of slurry containing 45% solids (on calcined basis), of which, 40% being SAPO-34 molecular sieve, 10.6% being alumina binder, and 49.4% being clay matrix material. The weight ratio of the binder to the molecular sieve is about 0.265 and a MSA of 489 m$^2$/g-molecular sieve.

Example 2

Spray drying of the slurry of Example 1 was conducted using a Yamato DL-41 spray dryer (Yamato Scientific America, Orangeburg, N.Y.). An amount of 750 g of the slurry was spray dried. The spray dryer operated in a down spray mode using an atomization nozzle of 1 mm. The spray drying conditions were: feed rate: 40 g/min; inlet temperature: 350° C.; atomization pressure: 14 psig (96.5 kPag); carrier gas (nitrogen) flow at 60% of full setting. The spray dry product, the formulated molecular sieve catalyst composition was collected in a cyclone. The catalyst composition was then calcined in a muffle furnace at 650° C. in air for 2 hours. The calcined catalyst composition was used for attrition testing and particle size analysis. Attrition resistance of the spray dried catalyst composition was determined using a jet-cup attrition unit. The hourly fines generation as a result of attrition thus obtained is defined as the ARI. The higher the ARI the higher the attrition rate or the weaker or softer the formulated molecular sieve catalyst composition. The molecular sieve catalyst composition of Example 1 spray dried in accordance with this Example 2 had an ARI of 0.95 weight percent per hour.

Example 3

A slurry containing 45 wt % solid (on calcined basis), 40% being SAPO-34 molecular sieve having not been fully dried or has not been calcined, 5.3% $Al_2O_3$ (the binder), and 54.7% clay (the matrix material), was prepared according to the procedure: (A) add 332.1 g of a SAPO-34 molecular sieve, the wet filtercake, (on a calcined basis of 180.01 g) (liquid medium content 34.72 weight percent based on the total weight of the molecular sieve and the liquid medium) to 201.82 g of deionized water that was mixed at 700 RPM using a Yamato 4000D mixer (Yamato Scientific America Inc., Orangeburg, N.Y.) for 10 minutes, then followed by a high-shear treatment using the Silverson high shear mixer at 6000 RPM for 3 minutes. This slurry had a pH value of 6.9 measured at 30° C. (B) ACH-Solution: add 48.28 g (on a calcined basis of 23.85 g) of Reheis MicroDry aluminum chlorohydrate (Reheis Inc., Berkeley Heights, N.J.) to 100.91 g of deionized water and mixed at 700 RPM using a Yamato 4000D mixer (Yamato Scientific America Inc., Orangeburg, N.Y.) for 7 minutes, and then followed by a high-shear treatment using the Silverson high shear mixer at 6000 RPM for 3 minutes. This solution had a pH of 4.0 measured at 25° C. (C) the above SAPO-34 slurry (A) and aluminum chlorohydrate solution (B) were combined, and mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry had a pH value of 4.2 measured at 30° C. (D) add 283.28 g (on a calcined basis of 246.16 g) of Engelhard's ASP Ultrafine kaolin clay (the matrix material) (Engelhard Corporation, Iselin, N.J.) to the above slurry containing SAPO-34 molecular sieve and aluminum chlorohydrate (the binder) under constant mixing at 250 to 400 RPM then mixed at 700 RPM using a Yamato 4000D mixer (Yamato Scientific America Inc., Orangeburg, N.Y.) for 10 minutes, and followed by a high-shear mixing step using the Silverson mixer at 6000 RPM for 3 minutes. (E) the solid content of the slurry was adjusted to contain 45% solids, an amount of 33.64 g of deionized water was added to the above slurry containing SAPO-34 molecular sieve, ACH solution, and kaolin clay followed with 700 RPM treatment for 15 minutes using the Yamato mixer, and subsequent high-shear mixing using the Silverson mixer at 6000 RPM for 3 minutes. This final slurry had a pH value of 4.2 measured at 27° C. This led to 1000 g of slurry containing 45% solids (on calcined basis), of which, 40% being SAPO-34 molecular sieve, 5.3% being alumina binder, and 54.7% being clay matrix material. The slurry of this Example 3 was then spray dried using the same procedure described in Example 2, in which the slurry of Example 1 was replaced with the slurry of Example 3. The molecular sieve catalyst composition of Example 3 spray dried in accordance with Example 2 had an ARI of 5.77 weight percent per hour. The weight ratio of the binder to the molecular sieve is about 0.13 and a MSA of 511 m²/g-molecular sieve.

Example 4

A slurry containing 45 wt % solid (on calcined basis), 40% being SAPO-34 molecular sieve having not been fully dried or has not been calcined, 15.9% $Al_2O_3$ (the binder), and 44.1% clay (the matrix material), was prepared according to the procedure: (A) add 332.1 g of a SAPO-34 molecular sieve, the wet filtercake, (on a calcined basis of 180.00 g) (liquid medium content 34.72 weight percent based on the total weight of the molecular sieve and the liquid medium), to 176.82 g deionized water and mixed at 700 RPM using a Yamato 4000D mixer (Yamato Scientific America Inc., Orangeburg, N.Y.) for 10 minutes, and then followed by a high-shear treatment using the Silverson high shear mixer at 6000 RPM for 3 minutes. This slurry had a pH value of 6.8 measured at 31° C. (B) ACH-Solution: add 144.84 g (on a calcined basis of 71.55 g) of Reheis Micro-Dry aluminum chlorohydrate (the binder) (Reheis Inc., Berkeley Heights, N.J.) to 88.41 g of deionized water, and mixed at 700 RPM using a Yamato 4000D mixer (Yamato Scientific America Inc., Orangeburg, N.Y.) for 7 minutes, and then followed by a high-shear treatment using the Silverson high shear mixer at 6000 RPM for 3 minutes. This solution had a pH of 3.1 measured at 32° C. (C) the above SAPO-34 molecular sieve slurry (A) and aluminum chlorohydrate solution (B) were combined, and mixed at 700 RPM using a Yamato 4000D mixer (Yamato Scientific America Inc., Orangeburg, N.Y.) for 10 minutes, then further mixed using the Silverson high-shear mixer at 6000 RPM for 3 minutes. This slurry had a pH value of 3.7 measured at 37° C. (D) add 228.37 g (on a calcined basis of 198.45 g) of Engelhard's ASP Ultrafine kaolin clay (Engelhard Corporation, Iselin, N.J.) to the above slurry containing SAPO-34 molecular sieve and aluminum chlorohydrate under constant mixing at 250 to 400 RPM was then mixed at 700 RPM using a Yamato 4000D mixer (Yamato Scientific America Inc., Orangeburg, N.Y.) for 10 minutes, and then followed by a high-shear mixing step using the Silverson mixer at 6000 RPM for 3 minutes. (E) the solid content of the slurry was adjusted to contain 45% solids, an amount of 29.47 g of deionized water was added to the above slurry containing SAPO-34 molecular sieve, ACH solution, and kaolin clay followed with 700 RPM treatment for 15 minutes using the Yamato mixer, and subsequent high-shear mixing using the Silverson mixer at 6000 RPM for 3 minutes. This final slurry had a pH value of 3.8 measured at 33° C. This led to 1000 g of slurry containing 45% solids (on calcined basis), of which, 40% being SAPO-34 molecular sieve, 15.9% being alumina binder, and 44.1% being clay matrix material. The slurry of this Example 4 was then spray dried using the same procedure described in Example 2, in which the slurry of Example 1 was replaced with the slurry of Example 4. The molecular sieve catalyst composition of Example 4 spray dried in accordance with Example 2 had an ARI of 0.38 weight percent per hour. The weight ratio of the binder to the molecular sieve is about 0.40 and a MSA of 470 m²/g-molecular sieve.

Example 5

A slurry containing 45 wt % solid (on calcined basis), 60% being SAPO-34 molecular sieve having not been fully dried or has not been calcined, 7.1% $Al_2O_3$ (the binder), and 32.9% clay (the matrix material), was prepared according to the procedure: (A) add 498.15 g of a SAPO-34 molecular sieve, the wet filter cake, (on a calcined basis of 270.00 g) (liquid medium content 34.72 weight percent based on the total weight of the molecular sieve and the liquid medium) to 160.08 g of deionized water, and then mixed at 700 RPM using a Yamato 4000D mixer (Yamato Scientific America Inc., Orangeburg, N.Y.) for 10 minutes, and then followed by a high-shear treatment using the Silverson high shear mixer at 6000 RPM for 3 minutes. This slurry had a pH value of 6.6 measured at 30° C. (B) ACH-Solution: add 64.68 g (on a calcined basis of 31.95 g) of Reheis MicroDry aluminum chlorohydrate (the binder) (Reheis Inc., Berkeley Heights, N.J.) to 80.04 g of deionized water, and then mixed at 700 RPM using a Yamato 4000D mixer (Yamato Scientific America Inc., Orangeburg, N.Y.) for 7 minutes, and then followed by a high-shear treatment using the Silverson high shear mixer at 6000 RPM for 3 minutes. This solution had a pH of 3.6 measured at 26° C. (C) the above SAPO-34 molecular sieve slurry (A) and aluminum chlorohydrate solution (B) were combined, and then mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry had a pH value of 4.1 measured at 32° C. (D) add 170.37 g (on a calcined basis of 148.05 g) of Engelhard's ASP Ultrafine kaolin clay (Engelhard Corporation, Iselin, N.J.) to the above slurry containing SAPO-34 molecular sieve and aluminum chlorohydrate (the binder) under constant mixing at 250 to 400 RPM, and then mixed at 700 RPM using a Yamato 4000D mixer (Yamato Scientific America Inc., Orangeburg, N.Y.) for 10 minutes, and then followed by a high-shear mixing step using the Silverson mixer at 6000 RPM for 3 minutes. (E) the solid content of the slurry was adjusted to contain 45% solids, an amount of 26.68 g of deionized water was added to the above slurry containing SAPO-34 molecular sieve, ACH solution, and kaolin clay followed with 700 RPM treatment for 15 minutes using the Yamato mixer, and subsequent high-shear mixing using the Silverson mixer at 6000 RPM for 3 minutes. This final slurry had a pH value of 3.9 measured at 32° C. This led to 1000 g of slurry containing 45% solids (on calcined basis), of which, 40% being SAPO-34 molecular sieve, 7.1% being alumina binder, and 32.9% being clay matrix material. The slurry of this Example 5 was then spray dried using the same procedure described in Example 2, in which the slurry of Example 1 was replaced with the slurry of Example 5. The molecular sieve catalyst composition of Example 5 spray dried in accordance with Example 2 had an ARI of 12.54 weight percent per hour. The weight ratio of the binder to the molecular sieve is about 0.12 and a MSA of 508 $m^2$/g-molecular sieve.

Example 6

A slurry containing 45 wt % solid (on calcined basis), 20% being SAPO-34 molecular sieve having not been fully dried or has not been calcined, 14.1% $Al_2O_3$ (the binder), and 65.9% clay (the matrix material), was prepared according to the procedure: (A) add 166.05 g of a SAPO-34 molecular sieve, the wet filtercake, (on a calcined basis of 90.00 g) (liquid medium content 34.72 weight percent based on the total weight of the molecular sieve and the liquid medium) to 218.55 g of deionized water, mixed at 700 RPM using a Yamato 4000D mixer (Yamato Scientific America Inc., Orangeburg, N.Y.) for 10 minutes, and followed by a high-shear treatment using the Silverson high shear mixer at 6000 RPM for 3 minutes. This slurry had a pH value of 6.8 measured at 25° C. (B) ACH-Solution: add 128.44 g (on a calcined basis of 63.45 g) of Reheis MicroDry aluminum chlorohydrate (the binder) (Reheis Inc., Berkeley Heights, N.J.) to 109.28 g of deionized water, and then mixed at 700 RPM using a Yamato 4000D mixer (Yamato Scientific America Inc., Orangeburg, N.Y.) for 7 minutes, and then followed by a high-shear treatment using the Silverson high shear mixer at 6000 RPM for 3 minutes. This solution had a pH of 3.5 measured at 28° C. (C) the above SAPO-34 molecular sieve slurry (A) and aluminum chlorohydrate solution (B) were combined, and mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry had a pH value of 4.0 measured at 28° C. (D) add 341.25 g (on a calcined basis of 296.55 g) of Engelhard's ASP Ultrafine kaolin clay (Engelhard Corporation, Iselin, N.J.) to the above slurry containing SAPO-34 molecular sieve and aluminum chlorohydrate under constant mixing at 250 to 400 RPM, and then mixed at 700 RPM using a Yamato 4000D mixer (Yamato Scientific America Inc., Orangeburg, N.Y.) for 10 minutes and then followed by a high-shear mixing step using the Silverson mixer at 6000 RPM for 3 minutes. (E) the solid content of the slurry was adjusted to contain 45% solids, an amount of 36.43 g of deionized water was added to the above slurry containing SAPO-34 molecular sieve, ACH Solution, and kaolin clay followed with 700 RPM treatment for 15 minutes using the Yamato mixer and subsequent high-shear mixing using the Silverson mixer at 6000 RPM for 3 minutes. This final slurry had a pH value of 3.7 measured at 31° C. This led to 1000 g of slurry containing 45% solids (on calcined basis), of which, 40% being SAPO-34 molecular sieve, 14.1% being alumina binder, and 65.9% being clay matrix material. The slurry of this Example 6 was then spray dried using the same procedure described in Example 2, in which the slurry of Example 1 was replaced with the slurry of Example 6. The molecular sieve catalyst composition of Example 6 spray dried in accordance with Example 2 had an ARI of 0.33 weight percent per hour. The weight ratio of the binder to the molecular sieve is about 0.71 and a MSA of 482 $m^2$/g-molecular sieve.

Example 7

Conversion Process

Catalytic performance of a molecular sieve catalyst composition for conversion of methanol was conducted using a micro-reactor unit. Reaction conditions employed were: feed rate of 100 g-methanol per gram of molecular sieve; temperature of 475° C.; pressure of 25 psig (273 kpag). A 35 mg of a catalyst composition of 2 to 200 microns in size mixed with 100 mg of silicon carbide (100 microns, available from Carborundum Abrasives G.B. Limited, Trafford Park, Manchester, UK) to form a mixture. This mixture was then loaded into a tubular reactor made of 316 stainless steel with an internal diameter of 4 mm. The catalyst composition bed is positioned in the middle section of the reactor by two quartz wool plugs on top and bottom of the catalyst composition bed. The catalyst composition was then treated in a helium flow at 50 $cm^3$/min (STP) from 40° C. to 475° C. at ramp rate of 100° C./min and held at 475° C. for 30 minutes before the methanol was introduced. Methanol (Fisher Scientific, Fair Lawn, N.J., 99.9% purity) is fed into a vaporizer kept at 225° C. by a Cole-Palmer 74900 Series syringe pump at a feed rate of 29.59 ml per minute. Methanol flow was down flowed through the heated reactor tube. Gas phase products and unreacted methanol were combined with 50 $cm^3$/min (STP) helium at the outlet and periodic samples were captured in an on-line sample storage (16-loop, 150 ml/loop) valve. All the transfer lines and sampling valves were heat traced to 225° C. to prevent any condensation of unreacted methanol or products. The collected samples were then analyzed using an on-line GC (Hewlett Packard 6890 GC, Palo Alto, Calif.) equipped with an FID detector and a PLOT fused silica column (CP-PoraPLOT Q, 10 m×0.53 mm ID×20 micron coating thickness, available from Varian, Inc, Mitchell Dr., Walnut Creek, Calif.). The reactor effluent was analyzed for: methane, methanol, dimethylether, ethane, ethylene, propane, propylene, isobutane, butene-1, cis-butene-2, and trans-butene-2, $C_5$ and higher, $C_6$ and higher, $C_7$ and higher and $C_8$ and higher.

Conversion of methanol is defined as [($X_{CH3OH\ in\ feed}$ − $X_{CH3OH\ in\ product}$)/$X_{CH3OH\ in\ feed}$]*100%; selectivity to each product component is defined as ($X_{product}$/$X_{CH3OH\ in\ feed}$)*100, where X is the water free weight fraction of each component calculated from the FID signal. Coke selectivity was estimated from a hydrogen balance of the feed and products. The product selectivity results reported are conversion weighted averages of the product selectivity over the entire experiment that measures methanol conversion from an initial conversion of approximately 100% to a final conversion of approximately 10%.

Catalytic performance of the catalyst composition of Example 2 for conversion of methanol was evaluated using the process described above and showed a cumulative methanol converted per gram of molecular sieve of 12.6 g-methanol/g-molecular sieve and weight averaged ethylene and propylene selectivity of 75.2%.

Catalytic performance of the catalyst composition of Example 4 for conversion of methanol was evaluated using the process described above and showed a cumulative methanol converted per gram of molecular sieve of 11.4 g-methanol/g-molecular sieve and weight averaged ethylene and propylene selectivity of 74.3%.

Catalytic performance of the catalyst of Example 6 for conversion of methanol was evaluated using the process described and showed a cumulative methanol converted per gram of molecular sieve of 12.4 g-methanol/g-molecular sieve and weight averaged ethylene and propylene selectivity of 74.6%.

Example 8

(50% Sieve, Binder/Molecular Sieve Ratio of 0.265)

A slurry containing 45 wt % solid (on a calcined basis), 50% being SAPO-34 molecular sieve having not been fully dried or has not been calcined, 13.25% $Al_2O_3$ (alumina sol, the binder), and 36.75% clay (the matrix material), was prepared according to procedure: (A) add 334.9 g of a SAPO-34 molecular sieve, the wet filtercake, (on a calcined basis of 180.0 g) (liquid medium content 35.28 weight percent based on the total weight of the molecular sieve and the liquid medium) to 212.9 g of deionized water, and mixed at 700 RPM using a Yamato 4000D mixer (Yamato Scientific America Inc., Orangeburg, N.Y.) for 10 minutes, and then followed by a high-shear treatment using the Silverson high shear mixer at 6000 RPM for 3 minutes. This slurry had a pH value of 7.1 measured at 30° C. (B) add 96.9 g (on a calcined basis of 47.7 g) of Reheis MicroDry aluminum-chlorohydrate (Reheis Inc., Berkeley Heights, N.J.) the above SAPO-34 molecular sieve slurry (A), mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry (C) had a pH value of 4.0 measured at 30° C. (D) add 155.6 g (on a calcined basis of 132.3 g) of Engelhard's ASP Ultrafine kaolin clay (Engelhard Corporation, Iselin, N.J.) to the above slurry containing SAPO-34 molecular sieve and aluminum chlorohydrate under constant mixing at 250 to 400 RPM, and then mixed at 700 RPM using a Yamato 4000D mixer (Yamato Scientific America Inc., Orangeburg, N.Y.) for 10 minutes followed by a high-shear mixing step using the Silverson mixer at 6000 RPM for 3 minutes. This final slurry had a pH value of 3.9 measured at 38° C. This led to 800.0 g of slurry containing 45% solids (on calcined basis), of which, 50% being SAPO-34 molecular sieve, 13.25% being alumina binder, and 36.75% being clay matrix material. The weight ratio of the binder to the molecular sieve is about 0.265 and a MSA of 498 $m^2$/g-molecular sieve.

Example 9

Spray drying of the slurry of Example 8 was conducted using a Yamato DL-41 spray dryer (Yamato Scientific America, Orangeburg, N.Y.). An amount of 800 g of the slurry was spray dried. The spray dryer operated in a down spray mode using an atomization nozzle of 1 mm. The spray drying conditions were: feed rate: 40 g/min; inlet temperature: 350° C.; atomization pressure: 14 psig (96.5 kpag); carrier gas (nitrogen) flow at 60% of full setting. The spray dry product, the formulated molecular sieve catalyst composition was collected in a cyclone. The catalyst composition was then calcined in a muffle furnace at 650° C. in air for 2 hours. The calcined catalyst composition was used for attrition testing and particle size analysis. Attrition resistance of the spray dried catalyst composition was determined using a jet-cup attrition unit. The hourly fines generation as a result of attrition thus obtained is defined as the ARI. The higher the ARI the higher the attrition rate or the weaker or softer the formulated molecular sieve catalyst composition. The molecular sieve catalyst composition of Example 8 spray dried in accordance with Example 9 had an ARI of 0.24 weight percent per hour.

Example 10

(60% Sieve, Binder/Molecular Sieve Ratio of 0.265)

A slurry containing 45 wt % solid (on a calcined basis), 60% being SAPO-34 molecular sieve having not been fully dried or has not been calcined, 15.9% $Al_2O_3$ (alumina sol, the binder), and 24.1% clay (the matrix material), was prepared according to procedure: (A) add 854 g of a SAPO-34 molecular sieve, the wet filtercake, (on a calcined basis of 459 g) (liquid medium content 35.28 weight percent based on the total weight of the molecular sieve and the liquid medium) to 383 g of deionized water, and mixed at 700 RPM using a Yamato 4000D mixer (Yamato Scientific America Inc., Orangeburg, N.Y.) for 10 minutes, and then followed by a high-shear treatment using the Silverson high shear mixer at 6000 RPM for 3 minutes. This slurry had a pH value of 6.5 measured at 29° C. (B) add 246.2 (on a calcined basis of 121.64 g) of Reheis MicroDry aluminum chlorohydrate (Reheis Inc., Berkeley Heights, N.J.) the above SAPO-34 molecular sieve slurry (A), mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry (C) had a pH value of 3.54 measured at 30° C. (D) add 216.8 g (on a calcined basis of 184.37 g) of Engelhard's ASP Ultrafine kaolin clay (Engelhard Corporation, Iselin, N.J.) to the above slurry containing SAPO-34 molecular sieve and aluminum chlorohydrate under constant mixing at 250 to 400 RPM, and then mixed at 700 RPM using a Yamato 4000D mixer (Yamato Scientific America Inc., Orangeburg, N.Y.) for 10 minutes followed by a high-shear mixing step using the Silverson mixer at 6000 RPM for 3 minutes. This final slurry had a pH value of 3.5 measured at 33° C. This led to 1700.0 g of slurry containing 45% solids (on calcined basis), of which, 60% being SAPO-34 molecular sieve, 15.9% being alumina binder, and 24.1% being clay matrix material. The weight ratio of the binder to the molecular sieve is about 0.265 and a MSA of 499 $m^2$/g-molecular sieve.

Example 11

Spray drying of the slurry of Example 10 was conducted using a Yamato DL-41 spray dryer (Yamato Scientific America, Orangeburg, N.Y.). An amount of 850 g of the slurry was spray dried. The spray dryer operated in a down spray mode using an atomization nozzle of 1 mm. The spray drying conditions were: feed rate: 40 g/min; inlet temperature: 350° C.; atomization pressure: 14 psig (96.5 kPag); carrier gas (nitrogen) flow at 60% of full setting. The spray dry product, the formulated molecular sieve catalyst composition was collected in a cyclone. The catalyst composition was then calcined in a muffle furnace at 650° C. in air for 2 hours. The calcined catalyst composition was used for attrition testing and particle size analysis. Attrition resistance of the spray dried catalyst composition was determined using a jet-cup attrition unit. The hourly fines generation as a result of attrition thus obtained is defined as the ARI. The higher the ARI the higher the attrition rate or the weaker or softer the formulated molecular sieve catalyst composition. The molecular sieve catalyst composition of Example 10 spray dried in accordance with Example 11 had an ARI of 0.23 weight percent per hour.

Example 12

A slurry containing SAPO-34, alumina binder and clay as a matrix was prepared according to the following procedure: (A) 332.1 g of a SAPO-34 molecular sieve filtercake (partially dried molecular sieve, one that has not been fully calcined) (liquid medium content 34.72 weight percent based on the total weight of the molecular sieve and the liquid medium) was added to 189.32 g of deionized water and mixed at 1000 RPM using a Yamato 4000D mixer (Yamato Scientific America Inc., Orangeburg, N.Y.) for 2 minutes. This SAPO-34 slurry gave a pH value of 6.4 measured at 22° C. (B) An aluminum chlorohydrate solution was prepared by adding 96.56 g of Reheis MicroDry aluminum chlorohydrate (Reheis Inc., Berkeley Heights, N.J.) to 94.66 g of deionized water and mixed at 1000 RPM using a Yamato 4000D mixer (Yamato Scientific America Inc., Orangeburg, N.Y.) for 2 minutes. This solution had a pH of 3.8 measured at 26° C. (C) The SAPO-34 slurry prepared in step (A) and aluminum chlorohydrate solution prepared in step (B) were mixed at 1000 RPM using a Yamato 4000D mixer (Yamato Scientific America Inc., Orangeburg, N.Y.) for 2 minutes. This second slurry had a pH value of 4.3 measured at 23° C. (D) 255.81 g of Engelhard's ASP Ultrafine kaolin clay (Engelhard Corporation, Iselin, N.J.) were added to the second slurry obtained at step (C) under constant mixing at 250 to 300 RPM then mixed at 1000 RPM using a Yamato 4000D mixer (Yamato Scientific America Inc., Orangeburg, N.Y.) for 2 minutes. This third slurry had a pH value of 4.2 measured at 23° C. (E) 31.55 of deionized water was added to this third slurry obtained in step (D) then mixed at 1000 RPM using a Yamato 4000D mixer (Yamato Scientific America Inc., Orangeburg, N.Y.) for 2 minutes. The resulting 1000 g of the slurry of the invention contained 45% solids (on a calcined basis), of which, 40% being SAPO-34 molecular sieve, 10.6% being alumina binder, and 49.4% being clay matrix material.

Particle size analysis results obtained on a Microtrac S3000 instrument showed bimodal particle size distribution with the peaks centered at 0.9 micron and 5 microns respectively. The particle distribution of the slurry is given in Table 1.

TABLE 1

| Percentiles | Particle Size (micron) |
|---|---|
| 10% | 0.754 |
| 20% | 0.801 |
| 30% | 0.833 |
| 40% | 0.859 |
| 50% | 0.883 |
| 60% | 0.908 |
| 70% | 0.936 |
| 80% | 0.971 |
| 90% | 4.990 |
| 95% | 6.143 |

Example 13

The slurry obtained in Example 12 was treated using a Silverson high-shear mixer at 6000 RPM for 3 minutes (Silverson Machines, Inc., East Longmeadow, Mass.). Particle size analysis results obtained on a Microtrac S3000 instrument also showing a bimodal particle size distribution with the peaks centered at 0.9 micron and 5 microns respectively. The particle size distribution of this slurry is shown in Table 2.

TABLE 2

| Percentiles | Particle Size (micron) |
|---|---|
| 10% | 0.561 |
| 20% | 0.662 |
| 30% | 0.724 |
| 40% | 0.775 |
| 50% | 0.823 |
| 60% | 0.869 |
| 70% | 0.919 |
| 80% | 0.981 |
| 90% | 1.102 |
| 95% | 4.243 |

In this Example 13 the amount of particles greater than 4 microns was approximately 6% representing about 50% reduction in particles larger than 3 microns when compared to the data presented in Table 1. Moreover, the result shows a significant size reduction for the entire particle size range demonstrating the benefit of high-shear mixing in controlling particle sizes.

Example 14

The slurry was prepared according to Example 12, further mixed with a Yamato 4000D mixer at 200 RPM for 10 minutes at 200 RPM, and the slurry prepared according to Example 13 were introduced to a spray dryer and spray dried according to the following procedure. Spray drying of the slurries was conducted using a Yamato DL-41 spray dryer (Yamato Scientific America, Orangeburg, N.Y.). An amount of 750 g of the each slurry was spray dried. The spray dryer operated in a down spray mode using an atomization nozzle of 1 mm. The spray drying conditions were: feed rate: 40 g/min; inlet temperature: 350° C.; atomization pressure: 1 bar (metric units); carrier gas (nitrogen) flow at 60% of full setting. Spray dry products were collected in a cyclone. They were calcined in a muffle furnace at 650° C. in air for 2 hours. The calcined spray dried molecular sieve catalyst composition or formulated molecular sieve catalyst compositions of Examples 12 and 13 were tested for attrition and particle size distribution.

However, during spray drying of the slurry prepared in Example 12 plugging of the spray nozzle occurred due to the presence of lumpy materials in the slurry. Spray drying had to be interrupted three times to remove the spray nozzle and clean up the blockage. Attrition resistance of spray dried molecular sieve catalyst compositions of Examples 12 and 13 had an ARI of 2.51 percent per hour and 0.95 percent per hour respectively. The ARI was determined using the jet-cup attrition test described previously in this patent specification.

Example 15

A slurry containing 45 wt % solid (on a calcined basis), 40% being SAPO-34 molecular sieve having not been fully dried or has not been calcined, 10.6% $Al_2O_3$ (alumina sol, the binder), and 49.4% clay (the matrix material), was prepared according to procedure: (A) add 527.3 g of a SAPO-34 molecular sieve, wet filtercake, (on a calcined basis of 306.0 g) (liquid medium content 30.12 weight percent based on the total weight of the molecular sieve and the liquid medium) to 337.4 of deionized water, and mixed at 700 RPM using a Yamato 4000D mixer (Yamato Scientific America Inc., Orangeburg, N.Y.) for 10 minutes, and then followed by a high-shear treatment using the Silverson high shear mixer at 6000 RPM for 5 minutes. This slurry had a pH value of 7.0 measured at 32° C. (B) add 164.1 g (on a calcined basis of 81.1 g) of Reheis MicroDry aluminum chlorohydrate (Reheis Inc., Berkeley Heights, N.J.) to 1168.7.6 g of de-ionized water, mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry (B) had a pH value of 3.5 measured at 37° C. (C) add Slurry (A) to Slurry (B), mixed at 700 RPM using a Yamato 4000D mixer (Yamato Scientific America Inc., Orangeburg, N.Y.) for 10 minutes, and then mixed using the Silverson high-shear mixer at 6000 RPM for 5 minutes. This slurry (C) had a pH value of 4.0 measured at 34° C. (D) add 446.2 g of Engelhard's ASP Ultrafine kaolin clay (Engelhard Corporation, Iselin, N.J., 377.8 g on a calcined basis) and 56.2 g of de-ionized water to the above Slurry (C) containing SAPO-34 molecular sieve and aluminum chlorohydrate under constant mixing at 200 to 400 RPM, and then mixed at 700 RPM using a Yamato 4000D mixer (Yamato Scientific America Inc., Orangeburg, N.Y.) for 10 minutes followed by a high-shear mixing step using the Silverson mixer at 6000 RPM for 3 minutes. This final slurry had a pH value of 4.1 measured at 35° C. This led to 1699.9 g of slurry containing 45% solids (on a calcined basis), of which, 40% being SAPO-SAPO-34 molecular sieve, 10.6% being alumina binder, and 49.4% being clay matrix material.

Example 16

Spray drying of the slurry of Example 15 was conducted using a Yamato DL-41 spray dryer (Yamato Scientific America, Orangeburg, N.Y.). An amount of 800 g of the slurry was spray dried. The spray dryer operated in a down spray mode using an atomization nozzle of 1 mm. The spray drying conditions were: feed rate: 40 g/min; inlet temperature: 350° C.; atomization pressure: 14 psig (96.5 kpag); carrier gas (nitrogen) flow at 60% of full setting. The spray dry product, the formulated molecular sieve catalyst composition was collected in a cyclone. The catalyst composition was then calcined in a muffle furnace at 650° C. in air for 2 hours. The calcined catalyst composition was used for attrition testing and particle size analysis. Attrition resistance of the spray dried catalyst composition was determined using a jet-cup attrition unit. The hourly fines generation as a result of attrition thus obtained is defined as the ARI. The higher the ARI the higher the attrition rate or the weaker or softer the formulated molecular sieve catalyst composition.

The molecular sieve catalyst composition of Example 15 was spray dried in accordance with this Example 16 had an ARI of 1.03 weight percent per hour.

Example 17

A slurry containing 45 wt % solid (on a calcined basis), 40% being SAPO-34 molecular sieve having been partially dried, 10.6% $Al_2O_3$ (alumina sol, the binder), and 49.4% clay (the matrix material), was prepared according to procedure: (A) add 483.7 g of a SAPO-34 molecular sieve dried at 60° C. for 3 hrs (on a calcined basis of 324.0 g) (liquid medium content 19.34 weight percent based on the total weight of the molecular sieve and the liquid medium) to 403.1 g of deionized water, and mixed at 700 RPM using a Yamato 4000D mixer (Yamato Scientific America Inc., Orangeburg, N.Y.) for 10 minutes, and then followed by a high-shear treatment using the Silverson high shear mixer at 6000 RPM for 3 minutes. This slurry had a pH value of 6.4 measured at 27° C. (B) add 173.8 g (on a calcined basis of 85.9 g) of Reheis MicroDry aluminum chlorohydrate (Reheis Inc., Berkeley Heights, N.J.) to 201.6 g of deionized water, mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry (B) had a pH value of 3.0 measured at 30° C. (C) add Slurry (B) to Slurry (A), mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry (C) had a pH value of 3.8 measured at 29° C. (D) add 470.6 g (on a calcined basis of 401.8 g) of Engelhard's ASP Ultrafine kaolin clay (Engelhard Corporation, Iselin, N.J.) and 67.2 g of de-ionized water to the above Slurry (C) containing SAPO-34 molecular sieve and aluminum chlorohydrate under constant mixing at 250 to 400 RPM, and then mixed at 700 RPM using a Yamato 4000D mixer (Yamato Scientific America Inc., Orangeburg, N.Y.) for 10 minutes followed by a high-shear mixing step using the Silverson mixer at 6000 RPM for 3 minutes. This final slurry had a pH value of 3.8 measured at 31° C. This led to 1800.0 g of slurry containing 45% solids (on calcined basis), of which, 40% being SAPO-34 molecular sieve, 10.6% being alumina binder, and 49.4% being clay matrix material.

The molecular sieve catalyst composition of Example 17 spray dried in accordance with Example 16 had an ARI of 0.75 weight percent per hour.

Example 18

A slurry containing 45 wt % solid (on a calcined basis), 40% being SAPO-34 molecular sieve having been partially dried, 10.6% $Al_2O_3$ (alumina sol, the binder), and 49.4% clay (the matrix material), was prepared according to procedure: (A) add 212.5 g of a SAPO-34 molecular sieve dried at 25° C. overnight (on a calcined basis of 144.0 g) (liquid medium content 18.40 weight percent based on the total weight of the molecular sieve and the liquid medium) to 301.1 g of deionized water, and mixed at 700 RPM using a Yamato 4000D mixer (Yamato Scientific America Inc., Orangeburg, N.Y.) for 10 minutes, and then followed by a high-shear treatment using the Silverson high shear mixer at 6000 RPM for 3 minutes. This slurry had a pH value of 5.9 measured at 29° C. (B) add 77.2 g (on a calcined basis of 38.2 g) of Reheis MicroDry aluminum chlorohydrate (Reheis Inc., Berkeley Heights, N.J.) to Slurry (A), mixed at 700 RPM using a Yamato 4000D mixer (Yamato Scientific America Inc., Orangeburg, N.Y.) for 10 minutes, and then mixed using the Silverson high-shear mixer at 6000 RPM for 3 minutes. This slurry (B) had a pH value of 3.3 measured at 33° C. (C) Add 209.2 g (on a calcined basis of 177.8 g) to the above Slurry (B) containing SAPO-34 molecular sieve and aluminum chlorohydrate under constant mixing at 250 to 400 RPM, and then mixed at 700 RPM using a Yamato 4000D mixer (Yamato Scientific America Inc., Orangeburg, N.Y.) for 10 minutes followed by a high-shear mixing step using the Silverson mixer at 6000 RPM for 3 minutes. This final slurry had a pH value of 3.4 measured at 33° C. This led to 800.0 g of slurry containing 45% solids (on calcined basis), of which, 40% being SAPO-34 molecular sieve, 10.6% being alumina binder, and 49.4% being clay matrix material.

The molecular sieve catalyst composition of Example 18 spray dried in accordance with Example 16 had an ARI of 1.03 weight percent per hour.

While the present invention has been described and illustrated by reference to particular embodiments, those of ordinary skill in the art will appreciate that the invention lends itself to variations not necessarily illustrated herein. For example, it is contemplated that the molecular sieve catalyst composition is useful in the inter-conversion of olefin(s), oxygenate to gasoline conversions reactions, malaeic anhydride, phthalic anyhdride and acrylonitrile formulation, vapor phase methanol synthesis, and various Fischer Tropsch reactions. It is further contemplated that a plug flow, fixed bed or fluidized bed process are used in combination, particularly in different reaction zones within a single or multiple reactor system. It is also contemplated the molecular sieve catalyst compositions described herein are useful as absorbents, adsorbents, gas separators, detergents, water purifiers, and other various uses such as agriculture and horticulture. Additionally contemplated the molecular sieve catalyst compositions include one or more other molecular sieves in combination. For this reason, then, reference should be made solely to the appended claims for purposes of determining the true scope of the present invention.

We claim:

1. A method for formulating a molecular sieve catalyst composition, the method comprising the steps of:
   (a) providing a synthesized molecular sieve having not been fully dried;
   (b) making a slurry of the synthesized molecular sieve, a binder, and optionally a matrix material such that the weight ratio of binder to molecular sieve is in the range of from 0.1 to 0.5; such that the slurry comprises solid particles and a liquid medium;
   (c) mixing said slurry until at least 90 percent by volume of the solid particles have a diameter of less than 20 μm; and
   (d) forming the slurry to produce a formulated molecular sieve catalyst composition.

2. The method of claim 1 wherein, the synthesized molecular sieve is synthesized from the combination of at least two of the group consisting of a silicon source, a phosphorous source and an aluminum source, optionally in the presence of a templating agent.

3. The method of claim 1 wherein the synthesized molecular sieve having not been fully dried comprises an amount of a liquid medium in the range of from about 20 weight percent to 70 weight percent based on the total weight of the molecular sieve and liquid medium.

4. The method of claim 1 wherein the weight ratio of the binder to the molecular sieve is in the range of from 0.11 to 0.48.

5. The method of claim 1 wherein the molecular sieve catalyst composition has a micropore surface area (MSA) on a contained molecular sieve basis of at least 70% of the MSA of the molecular sieve by itself.

6. The method of claim 1 which comprises the step of mixing the slurry until at least 90 percent by volume of the solid particles have a diameter of less than 10 μm.

7. The method of claim 1 wherein the slurry comprises in the range of from 30 percent to 50 percent by weight solid particles.

8. The method of claim 1 wherein the slurry in step (d) is formed by spray drying.

9. The method of claim 1 wherein the method further comprises a step (e) calcining the formulated molecular sieve catalyst composition after step (d).

10. A method for formulating a molecular sieve catalyst composition, the method comprising the steps of: (a) providing a synthesized molecular sieve in the presence of a first liquid medium; (b) introducing a binder in a weight ratio to molecular sieve in the range of from 0.1 to 0.5, and optionally a matrix material and/or a second liquid medium to form a slurry; and (c) mixing and forming the slurry to produce a formulated molecular sieve catalyst composition, wherein the slurry comprises solid particles and the synthesized molecular sieve is not fully dried prior to step (b) and wherein said slurry is mixed until at least 90 percent by volume of said solid particles have a diameter less than 20 μm.

11. The method of claim 10 wherein the first and second liquid medium is water.

12. The method of claim 10 wherein the amount of the first liquid medium is in the range of from about greater than 1 weight percent to 80 weight percent based on the total weight of the molecular sieve and first liquid medium.

13. The method of claim 10 wherein the method further comprises step (d) calcining the formulated molecular sieve catalyst composition.

14. The method of claim 10 wherein the weight ratio of the binder to the molecular sieve is in the range of from 0.11 to 0.48.

15. The method of claim 10 wherein the molecular sieve catalyst composition has a micropore surface area (MSA) of at least 80% on a contained molecular sieve basis of the MSA of the molecular sieve by itself.

16. The method of claim 10 wherein the slurry is mixed until at least 90 percent by volume of the solid particles have a diameter of less than 10 μm.

17. The method of claim 10 wherein the slurry comprises in the range of from 20 percent to 60 percent by weight solid particles.

18. The method of claim 10 wherein the weight ratio of the binder to the molecular sieve is in the range of from 0.12 to 0.5, the slurry comprises in the range of from 30 percent to 50 percent by weight solid particles, and wherein the synthesized molecular sieve has been partially dried.

19. The method of claim 10 wherein the synthesized molecular sieve is a silicoaluminophosphate, an aluminophosphate and/or a chabazite framework-type molecular sieve.

20. A method for making a formulated molecular sieve catalyst composition, the method comprising the steps of:
   (a) synthesizing with a liquid medium a molecular sieve from the combination of at least two of the group consisting of a silicon source, a phosphorous source and an aluminum source, optionally in the presence of a templating agent, to form a slurry;
   (b) removing the molecular sieve from the slurry;
   (c) drying the molecular sieve to a level of liquid medium in the range of from about greater than 1 weight percent to 80 weight percent liquid medium based on the total weight of the molecular sieve and liquid medium;
   (d) combining the molecular sieve with a binder in a weight ratio of binder to molecular sieve in the range of from 0.1 to 0.5, and optionally with a matrix material to make a formulation composition, the formulation composition comprising a liquid portion and a solid portion;

(e) mixing said formulation composition until at least 90 percent by volume of said solid portion contains solid particles having a diameter of less than 20 µm; and
(f) forming the formulation composition to form the formulated molecular sieve catalyst composition.

21. The method of claim 20 wherein in step (c) the molecular sieve is dried to a level of liquid medium in the range of from 20 weight percent to 60 weight percent liquid medium based on the total weight of the molecular sieve and liquid medium.

22. The method of claim 20 wherein in step (c) the molecular sieve is dried to a level of liquid medium in the range of from 40 weight percent to 60 weight percent liquid medium based on the total weight of the molecular sieve and liquid medium.

23. The method of claim 20 wherein in step (f) the formulation composition is formed by spray drying the formulation composition to form the formulated molecular sieve catalyst composition.

24. The method of claim 20 wherein in step (f) the formulation composition is calcined.

25. The method of claim 20 wherein the weight ratio of the binder to the molecular sieve is in the range of from 0.11 to 0.48.

26. The method of claim 20 wherein the formulation composition is mixed until at least 90 percent by volume of the solid portion contains solid particles having a diameter of less than 10 µm.

27. The method of claim 26 wherein the formulation composition comprises in the range of from 30 percent to 50 percent by weight solid particles in the solid portion.

28. The method of claim 20 wherein the liquid medium is water.

29. The method of claim 20 wherein the synthesized molecular sieve is a silicoaluminophosphate, an aluminophosphate and/or a chabazite framework-type molecular sieve.

30. A slurry comprising a formulation composition for making a molecular sieve catalyst composition, the formulation composition comprising:
(i) a solid portion comprising solid particles, the solid particles comprising:
(a) a binder, and optionally a matrix material; and
(b) a synthesized molecular sieve comprising a level of a liquid medium based on the total weight of the molecular sieve; and wherein the weight ratio of binder to molecular sieve is in the range of from 0.1 to 0.5 and
(c) wherein at least 90 percent by volume of said solid portion comprises solid particles having a diameter of less than 20 µm; and
(ii) a liquid portion.

31. The slurry of claim 30 wherein the synthesized molecular sieve is partially dried.

32. The slurry of claim 30 wherein the level of the liquid medium is in the range of from 40 weight percent to 60 weight percent based on the total weight of the liquid medium and the molecular sieve.

33. The slurry of claim 30 wherein the weight ratio of the binder to the molecular sieve is in the range of from 0.11 to 0.5.

34. The slurry of claim 30 wherein the molecular sieve catalyst composition has a micropore surface area (MSA) of at least 80% on a contained molecular sieve basis of the MSA of the molecular sieve by itself.

35. The slurry of claim 30 wherein at least 90 percent by volume of the solid particles have a diameter of less than 10 µm.

36. The slurry of claim 30 wherein the slurry comprises in the range of from 30 percent to 50 percent by weight solid particles.

37. The slurry of claim 30 wherein the synthesized molecular sieve is synthesized from the combination of at least one of the group consisting of a silicon source, a phosphorous source and an aluminum source, optionally in the presence of a templating agent.

38. The slurry of claim 30 wherein the synthesized molecular sieve has an avenge particle size of from 0.1 microns to 2 microns.

39. The slurry of claim 30 wherein the formulated molecular sieve catalyst composition is selected from one or more of the group consisting of: silicoaluminophosphate, an aluminophosphate and/or a chabazite framework-type molecular sieve.

40. A formulated calcined molecular sieve catalyst composition prepared by the method or claim 1 and comprising solid particles, the solid particles comprising a molecular sieve, a binder and optionally a matrix material, wherein (a) the weight ratio of the binder to the molecular sieve is in the range of from 0.15 to about 0.35, (b) the binder is present in an amount of between 2 weight percent to 50 weight percent, (c) the molecular sieve is present in an amount of between 5 weight to 80 weight percent, (c) the matrix material is present in an amount of between 0 weight percent and 90 weight percent, all weight percents based on the total weight of the molecular sieve catalyst composition, (d) the MSA of the formulated calcined molecular sieve catalyst composition ranges from about 400 $m^2$/g-molecular sieve to 600 $m^2$/g-molecular sieve, (e) the MSA of the formulated calcined molecular sieve catalyst composition is at least 80% on a contained molecular sieve basis of the MSA of the molecular sieve by itself; and (f) the formulated calcined molecular sieve catalyst composition has an ARI in the range of from 0 to 1.5 weight percent per hour.

41. The formulated calcined molecular sieve catalyst composition of claim 40 wherein the ARI is in the range of from about 0 to 1.0 weight percent per hour.

42. The formulated calcined molecular sieve catalyst composition of claim 40 wherein the ARI is in the range of from about 0 to 0.5 weight percent per hour.

43. The formulated calcined molecular sieve catalyst composition of claim 40 wherein the molecular sieve is synthesized from the combination from at least two of the group consisting of a silicon source, a phosphorous source and an aluminum source, optionally in the presence of a templating agent.

44. The formulated calcined molecular sieve catalyst composition of claim 40 wherein the weight ratio of the binder to the molecular sieve is in the range of from 0.2 to about 0.3, and binder is aluminum chlorohydrol.

45. The formulated calcined molecular sieve catalyst composition of claim 40 wherein the binder is present in an amount of between 5 and 50 weight percent.

46. The formulated calcined molecular sieve catalyst composition of claim 40 wherein the molecular sieve is present in an amount of between 20 and 80 weight percent.

* * * * *